US012661445B2

(12) United States Patent
Guhl et al.

(10) Patent No.: US 12,661,445 B2
(45) Date of Patent: Jun. 23, 2026

(54) DRIP CHAMBER INSERT FOR AN INFUSION DEVICE OF A MEDICAL INFUSION SYSTEM

(71) Applicant: B. Braun Melsungen AG, Melsungen (DE)

(72) Inventors: Torben Guhl, Melsungen (DE); Uwe Erik Schneider, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 966 days.

(21) Appl. No.: 17/799,325

(22) PCT Filed: Feb. 18, 2021

(86) PCT No.: PCT/EP2021/053942
§ 371 (c)(1),
(2) Date: Aug. 12, 2022

(87) PCT Pub. No.: WO2021/165352
PCT Pub. Date: Aug. 26, 2021

(65) Prior Publication Data
US 2023/0338642 A1      Oct. 26, 2023

(30) Foreign Application Priority Data

Feb. 19, 2020    (DE) ..................... 10 2020 202 123.6

(51) Int. Cl.
*A61M 5/14*          (2006.01)
*A61J 1/20*          (2006.01)
(Continued)

(52) U.S. Cl.
CPC .......... *A61M 5/1411* (2013.01); *A61J 1/2058* (2015.05); *A61M 5/162* (2013.01); *A61M 5/16813* (2013.01); *A61M 5/165* (2013.01)

(58) Field of Classification Search
CPC ................ A61M 5/1411; A61M 5/162; A61M 5/16813; A61M 5/165; A61J 1/2058
See application file for complete search history.

(56) References Cited

U.S. PATENT DOCUMENTS

| | | | |
|---|---|---|---|
| 2,784,733 A | * | 3/1957 | Martinez ................. A61M 5/40 |
| | | | 137/433 |
| 2005/0171491 A1 | | 8/2005 | Minh Miner et al. |
| 2019/0015600 A1 | | 1/2019 | Herrick et al. |

FOREIGN PATENT DOCUMENTS

| | | |
|---|---|---|
| DE | 602005001512 | 3/2008 |
| EP | 0059694 A1 | 9/1982 |

(Continued)

OTHER PUBLICATIONS

Sangofix with PrimeStop and Spin-Lock connector, Hygienic and simple application of blood products, B | Braun Sharing Expertise, B. Braun Melsungen AG, Nov. 2017, with translation, 2 pages.

(Continued)

*Primary Examiner* — Theodore J Stigell
(74) *Attorney, Agent, or Firm* — Christopher A. Rothe; CM Law

(57)          ABSTRACT

A drip chamber insert for insertion into a drip chamber to be connected to a medical infusion or transfusion device. The drip chamber insert has an open first front side, discharge openings in a second front side opposite the first front side, and an overflow opening. The overflow opening is positioned in a region extending from the first to the second front side. The drip chamber features a drip chamber bottom with an outlet channel. The drip chamber insert is positioned in the drip chamber with the second front side facing the drip chamber bottom. The drip chamber insert or the drip chamber is usable for preparing operation of a medical infusion or transfusion device without shutting off and reopening a (Continued)

connection to the drip chamber and/or without external pressurization of the interior of the drip chamber.

21 Claims, 2 Drawing Sheets

(51) Int. Cl.
    *A61M 5/162*       (2006.01)
    *A61M 5/165*       (2006.01)
    *A61M 5/168*       (2006.01)

(56)                   References Cited

FOREIGN PATENT DOCUMENTS

| | | | |
|---|---|---|---|
| EP | 1106193 | A1 | 6/2001 |
| EP | 1559442 | B1 | 8/2005 |
| KR | 100609608 | B1 | 8/2006 |
| WO | 2012057602 | A1 | 5/2012 |

OTHER PUBLICATIONS

Search Report received in International Application No. PCT/EP2021/053942 dated Jun. 1, 2021, with translation, 4 pages.
Search Report received in German Application No. 10 2020 202 123.6 dated Jan. 19, 2021, with translation, 16 pages.
Office Action received in Chinese Application No. 202180015971.1 dated Oct. 19, 2023, with translation, 25 pages.

* cited by examiner

DRIP CHAMBER INSERT FOR AN INFUSION DEVICE OF A MEDICAL INFUSION SYSTEM

CROSS-REFERENCE TO RELATED APPLICATIONS

This application is the United States national stage entry of International Application No. PCT/EP2021/053942, filed Feb. 18, 2021, and claims priority to German Application No. 10 2020 202 123.6, filed Feb. 19, 2020. The contents of International Application No. PCT/EP2021/053942 and German Application No. 10 2020 202 123.6 are incorporated by reference herein in their entireties.

FIELD

The invention relates to a drip chamber insert for insertion into a drip chamber connected to a medical infusion or transfusion device, which is formed as a hollow body with an at least partially open first front side, discharge openings in a second front side opposite the first front side and at least one overflow opening, wherein the at least one overflow opening is formed by the at least partially open first front side or is located within a shell arranged between the first and the second front side.

BACKGROUND

In infusion and transfusion therapy, medical infusion devices are used for pressure and gravity infusion. A well-known infusion device is available under the registered trademark INTRAFIX® Safeset from B. Braun. This is a special infusion device with an air barrier and ventilation function. The infusion device has a drip chamber with—in relation to an assembled functional state—in the region of an upper side a piercing spike for piercing into an infusion solution container and in the region of a lower side a drip chamber bottom which merges into an outlet channel which is connected to a hose line. A fluid filter acting as an air barrier is positioned at a distance above the drip chamber bottom. The hose line has a connector (patient connector) at an end opposite the outlet channel for connection to an infusion needle. By actuating a roller clamp located on the hose line, the flow of infusion solutions through the hose line can be optionally ensured or prevented.

As delivered, the connector is equipped with a protective cap, such as a cap available under the trademark PRIMESTOP™. with an integrated air-permeable, liquid-repellent membrane that prevents the leakage of infusion solutions and the entry of bacteria, but can allow air to escape from the system.

In preparation for infusion, the system must be ventilated. This procedure is performed in the following sequence. First, the roller clamp is closed. Then the piercing spike is pierced into the infusion solution container. By pressing the flexible lower part of the drip chamber several times, the liquid level is set in the drip chamber. This is followed by opening the roller clamp to vent the hose line.

This process is relatively laborious and must be performed manually with the associated risk of mishandling.

SUMMARY

It is the object of the invention to provide a drip chamber of the type mentioned above, which can be used easily and quickly and which reduces the risk of incorrect handling by the user such as nursing staff. According to a further object, the drip chamber is to be formed to reduce the risk of air embolisms when the drip chamber is used in a medical infusion system on a patient and/or to prevent uncontrolled leakage of the infusion solution from the patient connector when the roller clamp is open, where appropriate in combination with a cap, such as a cap available under the trademark PRIMESTOP™, for drip-free venting.

The drip chamber insert according to the invention is for insertion in a drip chamber which can be connected to a medical infusion or transfusion device. The drip chamber insert is formed as a hollow body and has an at least partially open first front side, one or more discharge openings in a second front side opposite the first front side, and at least one overflow opening. The at least one overflow opening is located laterally in any region of the shell extending from the first front side to the second front side; it is used to allow liquid located in the drip chamber insert to drain laterally, in addition to the discharge opening(s) in the second front side. The at least one overflow opening allows infusion or transfusion fluid to drain not only through the discharge openings in the second front side but simultaneously through the at least one overflow opening. This function is best ensured when the at least one overflow opening is spaced from the one or more discharge openings in the axial direction of the drip chamber insert, i.e., lateral drainage does not begin until the infusion or transfusion fluid rises in use in the drip chamber insert and has reached a level up to the at least one overflow opening.

According to the invention, in a first embodiment it is provided that the at least one overflow opening is located within a shell arranged between the first and the second front side; preferably the distance from the second front side (S2) is at least ⅓ H, further preferably in the range 0.4 H to 0.8 H, where H is the height of the drip chamber insert (1) measured as the distance from the first to the second front side. In particular, the at least one overflow opening is located approximately halfway between the first and second front sides, i.e. in the range about 0.5 H±10%.

In a further embodiment, the at least one overflow opening is formed by the at least partially open first front side, and/or the at least one overflow opening is formed as an extension of the opening of the at least partially open first front side. In other words, in this further embodiment, the opening located in the at least partially open first front side may extend into the shell at one or more locations along the circumference such that at least one notch is formed at the upper edge of the shell (i.e., at the edge adjacent to the second front side or in use upstream edge).

The drip chamber insert is advantageously formed in shape and size such that it can be used as an insert in conventional drip chambers, in particular in a lower region (lower part) of the conventional drip chamber—in relation to an assembled functional state. With respect to an assembled functional state, the first front side of the drip chamber insert is an upper face (located upstream in use) and the second front side is a lower face (located downstream in use). To prepare the drip chamber insert of an infusion, only the piercing part of a drip chamber with integrated drip chamber insert according to the invention is pierced into an infusion solution container. The infusion solution flows through the opening of the first front side as a result of gravity and accumulates in the drip chamber insert until the fill level reaches the at least one overflow opening. This is achieved in particular by the total area (discharge area) defined by the (i.e. all) discharge openings being smaller than the area defined by the at least one overflow opening (overflow area).

In the following, for ease of reading, the singular is omitted and only overflow openings are referred to, so that the term "overflow openings" is here synonymous with "at least one overflow opening".

After reaching the overflow openings, the fill level within the drip chamber remains constant at the level of the overflow openings. The outflow rate from the drip chamber insert (i.e. the sum of the outflow rates through the outflow openings and through the overflow openings) corresponds to the inflow rate of the infusion solution into the drip chamber insert. The discharge openings cause the drip chamber to empty completely towards the end of the infusion.

The present invention can make the infusion preparation process much simpler, more time efficient and safer by eliminating most of the preparation steps. In particular, the following steps for preparing the infusion device can be eliminated: Closing the roller clamp, pressing the flexible lower part of the drip chamber several times, and opening the roller clamp. Overall, the present invention greatly simplifies the handling of gravity-based (or drip chamber-based) medical infusion and transfusion devices, standardizes the filling of the drip chamber, and significantly reduces the risk of incorrect handling. Furthermore, the invention achieves the highest level of patient safety.

In a preferred embodiment, the discharge openings are formed round and/or have a diameter of 0.5 to 3 mm, preferably 0.8 to 2 mm and in particular 1.0 to 1.5 mm. The sieve-like design of the lower face of the drip chamber insert is intended, on the one hand, to ensure a smaller outflow rate in relation to the feed rate and thus an increase in the filling level in the drip chamber insert. On the other hand, complete emptying of the drip chamber together with the drip chamber insert is ensured.

In a preferred embodiment of the present invention, the overflow openings in the shell surface are formed elongated. In particular, the overflow openings are located within the shell at the same height of the hollow body in the region between the first and second front sides. In particular, the overflow openings are slit-shaped, which allow the infusion fluid to pass through substantially unimpeded without leading to a further increase in the filling level beyond the height of the overflow openings.

In a preferred embodiment of the present invention, the overflow openings arranged within the shell are spaced from the second front side, and optionally the overflow openings are spaced from the first front side. Due to the spacing, the overflow openings are located within the shell arranged between the first and the second front side.

In a further embodiment of the present invention, the hollow body is cylindrical in shape. Preferably, the hollow body tapers towards the second front side. For example, the hollow body may have the shape of a cylinder, a cone or a truncated cone in the external geometry. In a preferred embodiment of the present invention, the hollow body has a height, measured as the distance from the first to the second front side, of 1 to 10 cm, preferably 2 to 8 cm and in particular 3 to 6 cm, and/or has an outer diameter, measured at the level of the first front side and/or at the level of the second front side, of 0.5 to 5 cm, preferably 1 to 4 cm and in particular 2 to 3 cm. Such a drip chamber insert is based on known drip chamber lower parts in terms of geometry and dimensions and can thus be easily integrated into known drip chambers. Furthermore, it is preferred that the hollow body is formed with respect to the drip chamber in such a way that an intermediate space is formed between the outer shell of the drip chamber insert and the inner shell of a lower region of the drip chamber (drip chamber lower part) and/or between the outer second front side of the drip chamber insert and the inner side of the drip chamber bottom, in order to ensure unhindered flow of the infusion solution out of the drip chamber.

The drip chamber insert according to the invention can be formed in one piece and/or made of plastic, in particular hard plastic. This enables simple production by means of a 2-jaw tool.

The drip chamber insert can be presented ready for use, in particular it can be packed together with other infusion sets in a common package. Preferably, the administration is sterile.

The problem is further solved by a drip chamber for a medical infusion or transfusion device having a drip chamber bottom having an outlet channel for connections to a hose line, and a drip chamber insert as described above positioned in the drip chamber with the second end side facing the drip chamber bottom.

In a preferred embodiment of the invention, the drip chamber has a liquid filter. This is positioned in the drip chamber between the drip chamber bottom and the drip chamber insert, and preferably at a distance (e.g. by means of spacers) to the outlet channel. The liquid filter is formed in particular as an AirStop, in that it prevents air bubbles from escaping from the drip chamber into the outlet channel and in this way additionally reduces the risk of air embolism in the patient. Furthermore, the liquid filter is preferably capable of acting as a particle filter to prevent particles from passing through.

According to a further (independent) preferred embodiment of the invention, in order to ensure unobstructed drainage of the infusion solution from the drip chamber insert and further out of the drip chamber through the outlet channel, the outer shell of the drip chamber insert is at least partially spaced from the inner shell of the drip chamber. It is further preferred that the drip chamber insert is positioned at a distance from the bottom of the drip chamber or, if present, at a distance from the liquid filter in the drip chamber. For this purpose, spacers may be provided at the corresponding positions to be spaced. The distance can be, for example, 0.1 to 10 mm, preferably 0.2 to 5 mm and in particular 0.5 to 3 mm.

According to a further embodiment of the invention, the drip chamber further has a hose line connected to the outlet channel and having a connector for connection to an infusion or transfusion needle. Preferably, the connector is provided with a closure cap that separates the interior of the hose line from the environment by means of an air-permeable and water-repellent membrane. This measure achieves the greatest possible automation during preparation and, in particular, the greatest possible automation during venting of the infusion device.

There are no particular restrictions with regard to the geometry and dimensions of the drip chamber, so that conventional drip chambers can be combined with the drip chamber insert according to the invention. However, it is preferred that the geometries and dimensions of the drip chamber and the drip chamber insert are matched. For example, the drip chamber is preferably (also) cylindrical in shape and/or the drip chamber tapers towards the outlet channel where appropriate.

Another aspect of the present invention relates to the use of a drip chamber insert (as described herein) or a drip chamber (as described herein) for preparing a medical infusion or transfusion device without shutting off and reopening a connection provided on the patient side to the drip chamber and/or without externally pressurizing the interior of the drip chamber. The term connection provided on the patient side is understood to mean, in particular, the hose line connected to the outlet channel. The term "without external pressurization of the interior of the drip chamber" means that, apart from the force of gravity acting on the infusion solution, no further forces are exerted on the infusion solution and, in particular, no forces are exerted on the drip chamber itself, for example by (multiple) compression (e.g. manual pressing) of the drip chamber.

BRIEF DESCRIPTION OF THE DRAWING FIGURES

In the following, the invention is explained in more detail on the basis of an embodiment according to the invention as shown in the attached exemplary figures, without being limited thereto, of which:

DETAILED DESCRIPTION

Figure 1:
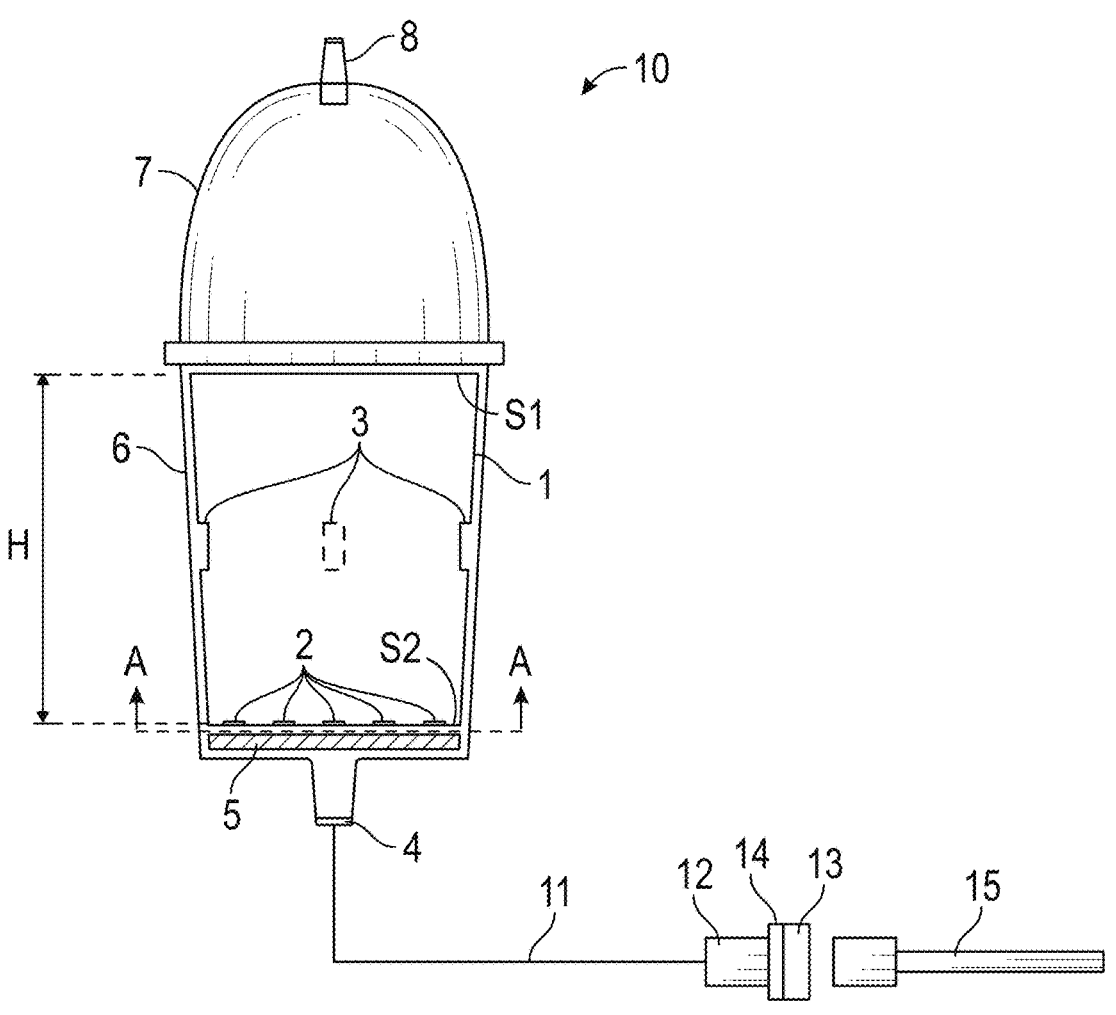
FIG. 1 is a sectional view of a drip chamber according to the invention with a drip chamber insert in a preferred embodiment.

FIG. 1 is a sectional view of a drip chamber according to the invention with a drip chamber insert according to a preferred embodiment of the invention. The drip chamber is a conventional cylindrical drip chamber 10 composed of lower part 6 and upper part 7. The lower part 6 is formed as a cylinder which tapers towards the outlet channel 4. The upper part 7 is shown here with a round or hemispherically tapering upper end with concentrically arranged piercing spike 8. A liquid filter 5 is located at the drip chamber bottom and preferably at a distance from the drip chamber bottom. Adjacent thereabove is a drip chamber insert 1 which substantially fills the lower part 6 except for a distance between the outer shell of the drip chamber insert 1 and the inner shell of the lower part 6, and between the bottom (outer side) of the drip chamber insert 1 and the bottom (inner side) of the drip chamber 10. In other words, a space is formed laterally and downward to the drip chamber in which infusion fluid can flow. For this purpose, the drip chamber insert 1 is adapted in size and shape to the lower part 6 of the drip chamber 10, i.e. corresponds to the geometry of the lower part 6 and is preferably slightly smaller. The drip chamber insert 1 has slot-shaped overflow openings 3 in its shell, in this embodiment preferably at about half the height. A plurality of discharge openings 2 are provided in the bottom of the drip chamber insert 1.

As shown schematically in FIG. 1, the drip chamber 10 may further have a hose line 11 connected to the outlet channel 4 with a connector 12 for connection to an infusion or transfusion needle 13. Preferably, the connector is provided with a closure cap 13 that separates the interior of the hose line from the environment by means of an air-permeable and water-repellent membrane 14.

Figure 2:
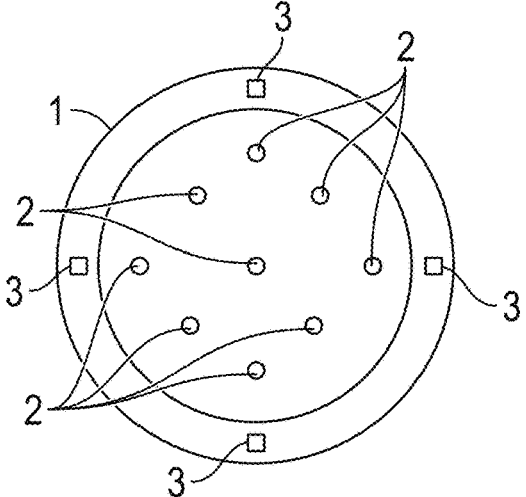
FIG. 2 is a view of the drip chamber insert of FIG. 1 in a view from below on front side in the sectional plane A-A of FIG. 1.

FIG. 2 shows a view of the drip chamber insert 1 from FIG. 1 (i.e. without showing the drip chamber 10) from below, specifically a top view from below of front side S2 in the sectional plane A-A in FIG. 1, but on a slightly larger scale than in FIG. 1. It is now even easier to see that the bottom of the drip chamber insert 1 has a large number of discharge openings 2 (shown here as round), preferably in a sieve structure. The sieve-like bottom allows a low flow rate due to relatively small discharge openings 2. Also shown are the slit-shaped overflow openings 3 located in the shell—approximately halfway up the conical/truncated spherical housing of the drip chamber insert 1. The overflow openings 3 allow a relatively high flow rate due to relatively large holes.

Figure 3:
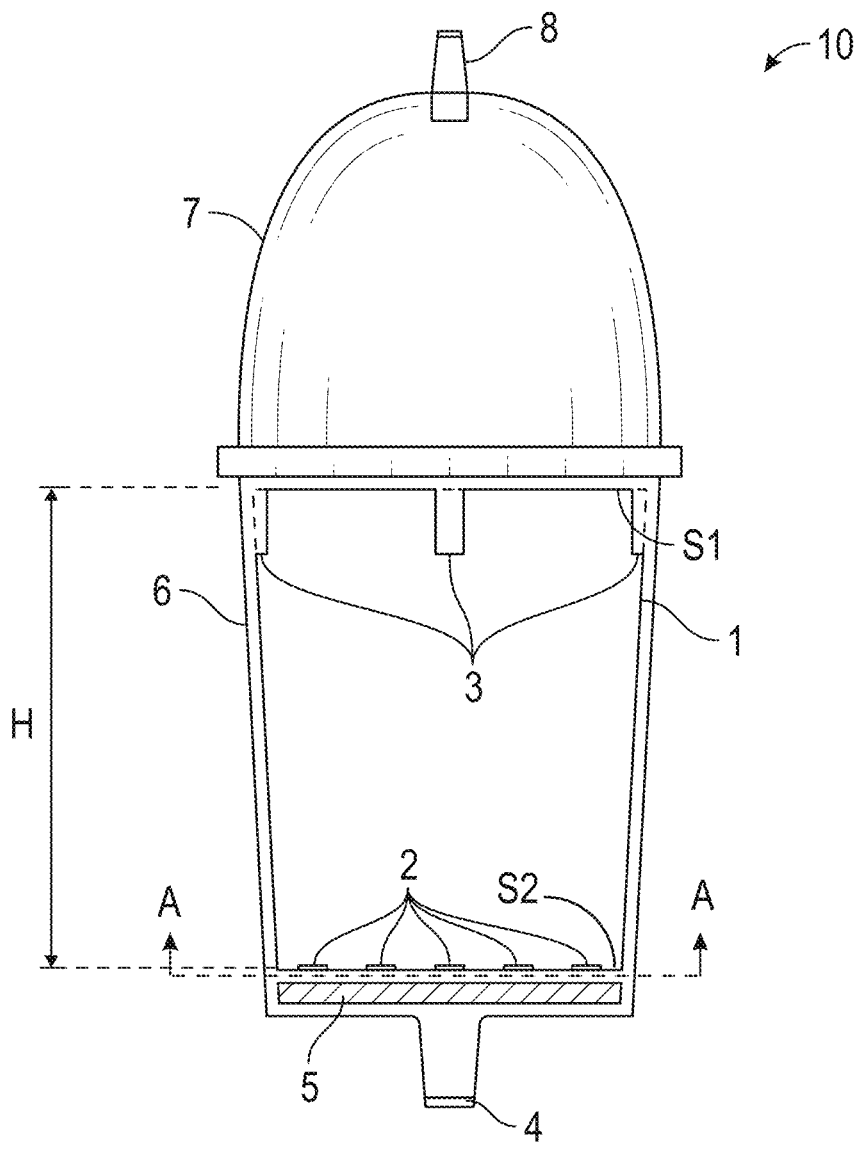
FIG. 3 is a sectional view of a drip chamber according to the invention with a drip chamber insert in a further embodiment.

FIG. 3 is a sectional view of another embodiment of the drip chamber according to the invention, showing a modification of the drip chamber insert of FIG. 1. In principle, the drip chamber is constructed in the same way as in FIG. 1, but with the difference that here the overflow openings 3 are not located in the shell between the first and second front sides S1, S2, but extend downwards away from the opening of the first front side S1 in the form of notches. The reference signs otherwise mean the same as in the embodiment according to FIG. 1.

The invention claimed is:

1. A drip chamber insert for insertion into a drip chamber to be connected to a medical infusion or transfusion device, wherein the drip chamber insert is formed as a hollow body and comprises:

a first front side that is at least partially open;

a second front side opposite the first front side, the second front side having discharge openings; and at least one overflow opening provided in a region of a shell of the hollow body extending from the first front side to the second front side;

wherein the shell comprises a continuous solid wall extending between the at least one overflow opening and the second front side.

2. The drip chamber insert according to claim 1, wherein:

i.) the at least one overflow opening is located in the region of the shell between the first front side and the second front side; or ii.) the at least one overflow opening is formed adjacent to the first front side; or iii.) the at least one overflow opening is provided in a region of an opening of the first front side or extends, at a plurality of points along a circumference, into the shell.

3. The drip chamber insert according to claim 1, wherein the at least one overflow opening extends into the shell by at least one notch extending from an upper edge of the shell at the first front side towards the second front side.

4. The drip chamber insert according to claim 1, wherein the at least one overflow opening is elongated in a direction from the first front side to the second front side.

5. The drip chamber insert according to claim 1, wherein the discharge openings have a round design and each discharge opening has a diameter of 0.5 mm to 3 mm.

6. The drip chamber insert according to claim 1, wherein the at least one overflow opening is spaced from the second front side and spaced from the first front side.

7. The drip chamber insert according to claim 6, wherein the at least one overflow opening is spaced from the second front side by a distance of at least $\frac{1}{3}$ H, wherein His a height of the drip chamber insert measured from the first front side to the second front side.

8. The drip chamber insert according to claim 6, wherein the at least one overflow opening is spaced from the second front side by a distance of between 0.4 H and 0.8 H, wherein His a height of the drip chamber insert measured from the first front side to the second front side.

9. The drip chamber insert according to claim 1, wherein a total discharge area defined by the discharge openings is smaller than a total overflow area defined by all of the at least one overflow opening.

10. The drip chamber insert according to claim 1, wherein the hollow body is cylindrical in shape and tapers towards the second front side.

11. The drip chamber insert according to claim 1, wherein the hollow body has at least one of:

i.) a height H, measured as a distance from the first front side to the second front side, of between 1 cm and 10 cm; and ii.) an outer diameter, measured at a level of the first front side and/or at a level of the second front side, of between 0.5 cm and 5 cm.

12. The drip chamber insert according to claim 1, wherein the drip chamber at least one of:

i.) comprises a plastic; and ii.) is sterile.

13. The drip chamber insert according to claim 1, wherein the drip chamber comprises a transparent hard plastic.

14. A drip chamber for a medical infusion or transfusion device comprising:

a drip chamber insert formed as a hollow body and comprising:

a first front side that is at least partially open;

a second front side opposite the first front side, the second front side having discharge openings; and at least one overflow opening provided in a region of a shell of the hollow body extending from the first front side to the second front side; and a drip chamber bottom having an outlet channel; and a liquid filter positioned at a distance from the outlet channel, wherein the drip chamber insert is positioned in the drip chamber with the second front side facing the drip chamber bottom.

15. The drip chamber according to claim 14, wherein the liquid filter is positioned between the outlet channel and the second front side of the drip chamber insert.

16. The drip chamber according to claim 14, wherein the liquid filter is configured to prevent air and/or particles from passing through the liquid filter.

17. The drip chamber according to claim 14, wherein the shell comprises a continuous solid wall extending between the at least one overflow opening and the second front side.

18. The drip chamber according to claim 14, further comprising a hose line connected to the outlet channel with a connector for connection to an infusion or transfusion needle, wherein the connector comprises a closure cap that separates an interior of the hose line from a surrounding environment by an air-permeable and water-repellent membrane.

19. The drip chamber according to claim 14, wherein a drip chamber lower part is cylindrical in shape and tapers towards the outlet channel.

20. The drip chamber according to claim 14, further comprising a piercing spike for piercing a container on a side opposite the drip chamber bottom.

21. A method for preparing operation of a medical infusion or transfusion device, the method comprising the steps of:

providing a drip chamber according to claim 14; and preparing operation of the medical infusion or transfusion device without shutting off and reopening a connection to the drip chamber on a patient side and/or without carrying out external pressurization of an interior of the drip chamber.

\* \* \* \* \*